US008156791B2

(12) United States Patent
Freeman

(10) Patent No.: US 8,156,791 B2
(45) Date of Patent: Apr. 17, 2012

(54) APPARATUS AND METHOD FOR TESTING RESERVOIR DRILLING FLUIDS FOR DRILLING UNCONSOLIDATED TAR SANDS

(75) Inventor: Michael A. Freeman, Kingwood, TX (US)

(73) Assignee: M-I L.L.C., Houston, TX (US)

( * ) Notice: Subject to any disclaimer, the term of this patent is extended or adjusted under 35 U.S.C. 154(b) by 229 days.

(21) Appl. No.: 12/748,038

(22) Filed: Mar. 26, 2010

(65) Prior Publication Data

US 2010/0199757 A1    Aug. 12, 2010

Related U.S. Application Data

(62) Division of application No. 11/679,265, filed on Feb. 27, 2007, now Pat. No. 7,716,968.

(60) Provisional application No. 60/777,178, filed on Feb. 27, 2006.

(51) Int. Cl.
*G01N 33/487* (2006.01)
(52) U.S. Cl. ........................................... 73/53.01
(58) Field of Classification Search .................. 73/53.01
See application file for complete search history.

(56) References Cited

U.S. PATENT DOCUMENTS

| 2,842,338 A | 7/1958 | Davis et al. |
| 3,934,455 A | 1/1976 | Harrisberger |
| 5,103,428 A | 4/1992 | Yale et al. |

*Primary Examiner* — Hezron E Williams
*Assistant Examiner* — Tamiko Bellamy
(74) *Attorney, Agent, or Firm* — Kimberly D. Ballew; Sara K. M. Hinkley; Patrick A. Traister

(57) ABSTRACT

An apparatus and method for testing fluids to be used when drilling in unconsolidated sand formations includes a container having a first port and a second port and a plurality of perforations through which fluid can be communicated, a bore holder slidingly retained through a portion of the container between the first port and the second port, wherein the bore holder has a feed end and a discharge end, a bed of unconsolidated sand contained in the container in a compacted state surrounding the bore holder, a fluid distribution nozzle at the discharge end of the bore holder, a fluid source in fluid communication with the discharge end of the bore holder, wherein the fluid source provides a test fluid to the fluid distribution nozzle through the bore holder, wherein the bore holder is withdrawn from the container at a predetermined speed as the test fluid is communicated through the fluid distribution nozzle, thereby leaving a simulated well bore in the unconsolidated sand.

4 Claims, 1 Drawing Sheet

APPARATUS AND METHOD FOR TESTING RESERVOIR DRILLING FLUIDS FOR DRILLING UNCONSOLIDATED TAR SANDS

The present application is a divisional application of U.S. patent application Ser. No. 11/679,265, filed on Feb. 27, 2007, now U.S. Pat. No. 7,716,968 which claims priority to Provisional U.S. Patent Application No. 60/777,178 filed on Feb. 27, 2006, entitled, "Apparatus and Method for Testing Reservoir Drilling Fluids for Drilling Unconsolidated Tar Sands," the contents of which are incorporated herein by reference.

BACKGROUND OF INVENTION

Many highly productive oil and gas fields are found in unconsolidated or poorly consolidated rock formations, that is, rock formations in which the individual grains of sand making up the rock formation have not yet become cemented together by the passage of time. Wells in these formations are normally "cased" by lining them with steel pipe. The casing is "perforated" by detonation of an explosive charge or the like within the pipe so as to form orifices in the casing at the depths where it is anticipated that oil and gas will be usefully recovered.

One of the problems encountered in obtaining oil or gas from a subsurface earth formation is unconsolidated sand, which can be carried into the well bore along with the oil or gas. This causes damage to equipment and also necessitates that the sand be removed from the oil or gas which is produced. Furthermore, excessive sand production can cause the entire formation to collapse, necessitating that the well be cleaned out and, in many cases, that it be packed with "gravel," a relatively coarser sand which then acts as a kind of filter. However, such methods are complex and expensive to perform. The problem can be alleviated by treating the formation sand with various chemicals to consolidate the sand particles. Before actual consolidation treatment is begun, a sample of the unconsolidated sand is tested for fluid permeability and other characteristics. The sample is then treated with the appropriate chemicals under simulated formation conditions. As new fluids and methods are developed, a test to effectively and efficiently determine the performance of the fluids and methods is required.

One prior procedure for the simulated test involves placing a container, such as a metal cylinder which is closed at one end, on a vibrating table. With the table vibrating, a volume of water, approximately 35% of the cylinder capacity, is placed in the cylinder, and the unconsolidated sand is sifted into the cylinder until it is full of moist, compacted sand. The open end of the cylinder is then capped and the sample is checked for fluid permeability, using a light oil at residual water saturation. The sand sample is then treated to consolidate the particles and the permeability of the sample to diesel oil is determined. However, this method has the drawback that the sand sample often includes clay, silt, or other non-sand fractions that segregate within the sample during the test, making it difficult to obtain an accurate flow profile of fluid through the sample. Further, the vibration technique used is often not reproducible among sand samples having different fractions of clay, silt and other non-sand components.

Another prior simulation technique involves placing an unconsolidated sand sample in a vessel and compacting the sample between two pistons. Fluids are passed through the compacted sample to determine flow permeability before and after a consolidating fluid is added to the sample.

One prior art test includes placing unconsolidated sands in a tube with a filter cake on one exposed surface of the sand. Fluid is pumped through the tube in each direction to measure the effectiveness of the filter cake and fluid. However, this prior art method does not effectively simulate the fluid flow as it would be found in the wellbore during drilling.

Another prior art method includes drilling through an artificially-created sand bed. While this method effectively simulates the drilling process, it is costly and requires a lot of equipment and space to perform.

It would be an improvement to the art to have a test apparatus and method that effectively simulates the drilling environment while not requiring the space and equipment of prior art testing methods.

SUMMARY

In one aspect, embodiments disclosed herein relate to an apparatus for simulating drilling conditions in unconsolidated tar sands. The apparatus includes a container having a inlet port and a outlet port and a plurality of perforations through which fluid can be communicated. A bore holder is slidingly retained through a portion of the container between the inlet port and the outlet port, wherein the bore holder has a feed end and a discharge end. A bed of unconsolidated sand is contained in the container in a compacted state surrounding the bore holder. A fluid distribution nozzle is located at the discharge end of the bore holder. A fluid source is in fluid communication with the discharge end of the bore holder, wherein the fluid source provides a test fluid to the fluid distribution nozzle through the bore holder. The bore holder is withdrawn from the container at a predetermined speed as the test fluid is communicated through the fluid distribution nozzle, thereby leaving a simulated well bore in the unconsolidated sand.

In another aspect, embodiments disclosed herein relate to a method for simulating drilling conditions. The method includes providing a bed of unconsolidated sand in a container through which a bore holder is slidably positioned, wherein the bore holder includes a fluid distribution nozzle at a discharge end and the container includes a plurality of perforations. The method further includes compacting the sample in the container and around the bore holder, controllably pumping a test fluid through the bore holder and the fluid distribution nozzle, withdrawing the bore holder from the container at a predetermined speed to create a simulated well bore, receiving a first portion of the test fluid from the simulated well bore in a line in fluid communication with the simulated well bore, and receiving a second portion of the test fluid from the perforations in the container.

Other aspects and advantages of the claimed subject matter will be apparent from the following description and the appended claims.

DESCRIPTION OF THE DRAWINGS

For a further understanding of the nature and objects of the present invention, reference should be made to the following detailed description taken in conjunction with the accompanying drawings, in which like parts are given the reference numerals, wherein.

DETAILED DESCRIPTION

In one aspect, embodiments disclosed herein relate to an apparatus and method for simulating drilling conditions in unconsolidated tar sands. Additionally, embodiments disclosed herein are directed to an apparatus and method for testing fluids, washout, and wellbore strengthening in an unconsolidated tar sand environment.

Figure 1:
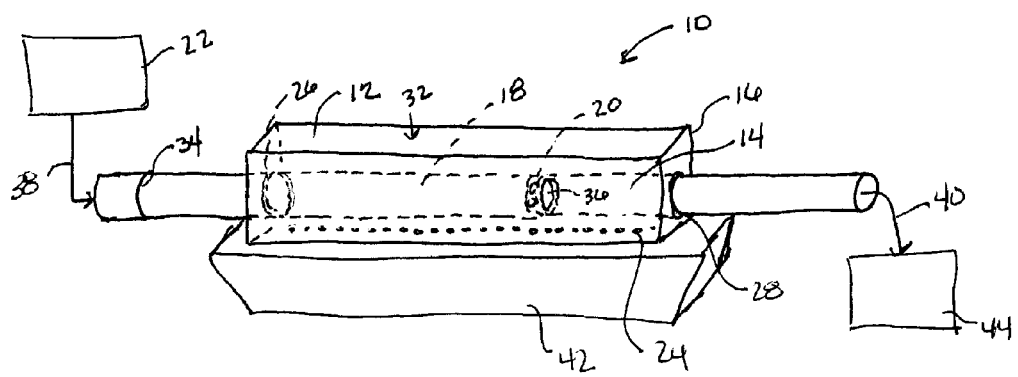
FIG. 1 is a schematic view of an unconsolidated sand well bore simulator according to embodiments disclosed herein.
Figure 2:
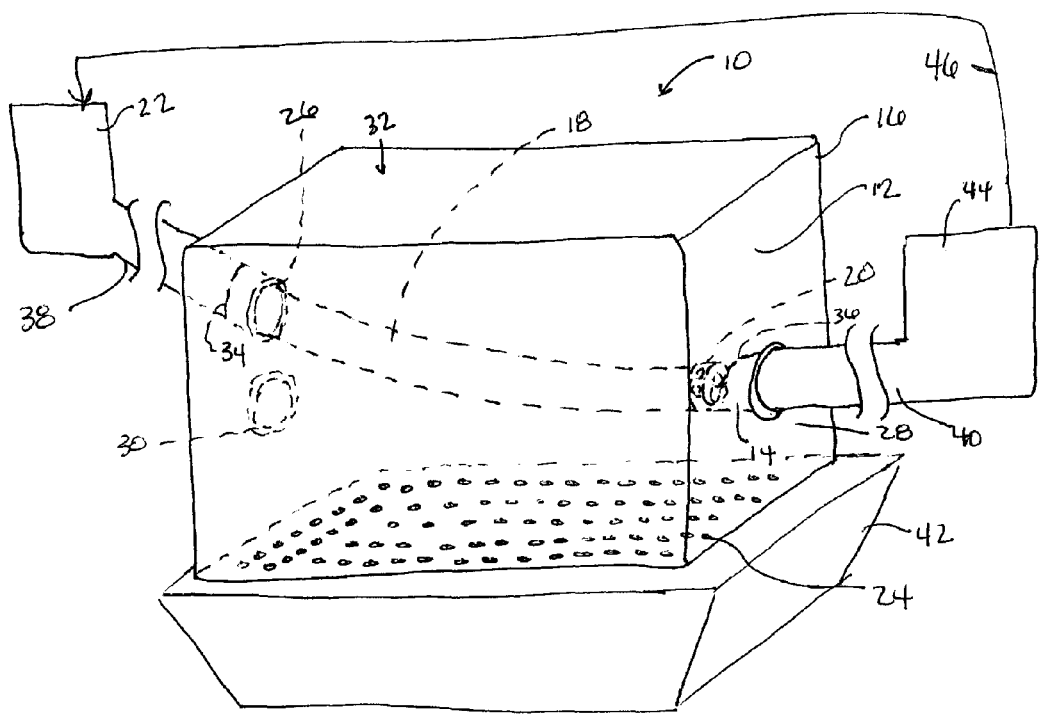
FIG. 2 is a schematic view of an unconsolidated sand well bore simulator according to embodiments disclosed herein.

Referring to FIG. 1, an apparatus for simulating a well bore in unconsolidated sand is shown generally as 10. The apparatus 10 includes a container 16. Container 16 may be a mesh box or a slotted liner or some other type of container including a plurality of perforations 24 through the wall or walls of the container to provide fluid communication between the inside and outside of the container 16. The perforations 24 depicted in FIGS. 1 and 2 are shown as small holes. One of skill in the art will appreciate that perforations 24 may be formed by using a wire mesh to form the container 16. The shape of the container 16 is depicted as a rectangular box, but one of skill in the art will appreciate that the shape of the container may be cylindrical, cubical, or even a non-symmetrical shape.

The container 16 includes an inlet port 26 and an outlet port 28. The inlet port 26 provides fluid communication between a test fluid source 22 and the container 16. The outlet port 28 provides fluid communication between the container 16 and a collection area 44. A fluid line 46 may connect the collection area 44 to the test fluid source 22 so that the test fluid may be circulated through the test apparatus 10.

A bore holder 18 is located through the container 16. The bore holder 18 is cylindrical in shape corresponding to the shape of a well bore. In one embodiment, the bore holder 18 is a cylindrical pipe. The bore holder 18 may be rigid or flexible. In one embodiment, such as that depicted in FIG. 1, the inlet port 26 and the outlet port 28 of the container 16 are located such that the bore holder 18 formed from a rigid pipe extends between the inlet and outlet ports 26 and 28 in an initial position. In another embodiment, such as that shown in FIG. 2, the container includes a port 30 located in a wall of the container 16 such that the bore holder 18 flexes between the port 30 and the outlet port 26 in an initial position. Various ports may be added to simulate various well bore configurations. As will be discussed, bore holder 18 can be slidably withdrawn from a port, such as inlet port 26.

Referring again to FIG. 1, the apparatus 10 includes a sand bed 12 through which a bore 14 has been created in a central portion by the bore holder 18. The sand bed 12 simulates the formation that is being drilled. In one embodiment, commercial sand and oil is used to simulate the formation. In one embodiment, recovered tar sand is used to simulate the formation. In one embodiment, the 'formation' will be created by slurry-packing the sand into the container 16 traversed by the bore holder 18.

The sand bed 12 is retained in the container 16 in a compacted state to simulate the pressures that would be experienced by the unconsolidated sand in the area that is being or will be drilled. In one embodiment, weight is applied to a top surface 32 of the sand bed 12 to compress the sand bed 12. One of experience in the art will appreciate that compression force may be applied in many ways, including compression band clamps, pistons, length adjustment joints, clamps, etc. The bore holder 18 prevents the simulated well bore from collapsing as the sand bed is compressed around it.

As previously discussed, the bore holder 18 extends between an inlet port 26 and outlet port 28 in the container 16 in an initial position. The bore holder 18 has a feed end 34 that will receive a test fluid. A discharge end 36 of the bore holder 18 is fitted with a fluid distribution nozzle 20. The fluid distribution nozzle 20 is configured to simulate the flow of fluid from a drill bit in the well bore. To achieve this, a fluid distribution nozzle 20 that radially distributes the test fluid is selected. The fluid distribution nozzle 20 may distribute some test fluid axially as well as radially.

The feed end 34 of bore holder 18 is initially positioned at an inlet port 26 within container 16. One of skill in the art will appreciate that the feed end 34 of bore holder 18 may be positioned initially at any port in container 16. The fluid distribution nozzle 20 at the distribution end 36 of the bore holder 18 will be at an outlet port 28, which may also be at another adjacent port. A fluid line 38 provides fluid communication between the fluid source 22 and the feed end 34 of the bore holder 18. When a fluid is tested, the bore holder 18 will be withdrawn at a predetermined speed from the inlet port 26. In one embodiment, the fluid line 38 is connected directly to the feed end 34 of the bore holder 18. In another embodiment, the fluid line 38 is connected to the inlet port 26 at which the feed end 34 of the bore holder 18 is initially located. As will be described, in this embodiment, the fluid line 38 is of a sufficient size to receive at least a portion of the bore holder 18 as it is withdrawn from the container 16. Another fluid line 40 provides fluid communication between an outlet port 28 and a collection area 44.

As the bore holder 18 is withdrawn from the container 16, a simulated well bore 14 will be left in the unconsolidated sand bed 12. Fluid is pumped through the bore holder 18 and the resulting well bore 14 at a predetermined volume flow rate. The well bore 14 is "drilled" as the bore holder 18 is withdrawn from the container 16. The withdrawal of the bore holder 18 from the container 16 may be effected by a linear motor, motor with a rack and pinion drive system, compressed air actuators, a magnetic drive system, or other systems known to those of skill in the art. As previously discussed, in one embodiment, the bore holder 18 is withdrawn into fluid line 38. In this embodiment fluid line 38 is of sufficient size and construction to receive at least a portion of the bore holder 18 into the area inside of the line.

A method for testing a fluid includes locating the bore holder 18 within the container 16 between the inlet port 26 and the outlet port 28. The fluid distribution nozzle 20 is located at the discharge end 36 of the bore holder 18. The fluid line 38 provides fluid communication between the fluid source 22 and the feed end 34 of the bore holder 18. The fluid line 40 provides fluid communication between the outlet port 28 and the collection area 44. The sand bed 12 of unconsolidated sand is prepared and placed in the container around the bore holder 18. The sand bed 12 is then compacted to simulate pressure in a down hole formation.

The sample fluid to be tested is provided by the fluid source 22. The test fluid is pumped into the feed end 34 of the bore holder 18, through the body of the bore holder 18 and through the fluid distribution nozzle 20 at a predetermined flow rate. The flow rate selected will correspond to the flow rate through an actual well bore that would be drilled. As the apparatus 10 may be scaled down to a smaller dimension, the selected flow rate will be calculated to match the scale of the test bore 14.

As the test fluid is circulated through the bore holder 18 and fluid distribution nozzle 20 to the outlet port 28, the bore holder 18 is withdrawn from the container 16 through the inlet port 26. When the bore holder 18 is withdrawn, the test bore 14 is formed in the unconsolidated sand. The bore holder 18 is withdrawn from the container at a predetermined speed corresponding to the rate at which a well bore is drilled and scaled, as needed, to match the size of the test apparatus 10 and resulting test bore 14.

Filtrate is free to flow out from the test bore 14 through the sand bed 12, exiting through the perforations 24. As the bore holder 18 is withdrawn, the countervailing influences of fluid drag washing out the fluid versus the stabilizing effect of a filter cake formation will determine the ultimate size of the test bore 14. In one embodiment, screen blinding, washout, hole cleaning and flowback through the perforations 24 in the container 16 are performance indicators of the test fluid. In one embodiment, washout and well bore collapse are measured by circulation through a simulated well bore. In one embodiment, after the flow experiment is complete, actual or simulated production liner (not shown) will be run through the test bore 14 and flow direction reversed.

In addition to testing fluids, the apparatus 10 can be used to test performance of fluids in a sample of unconsolidated sand from a formation. For example, fluid that exits through perforations 24 can be collected in a collection receptacle 42 and measured to determine flow permeability of the unconsolidated sand sample.

While the claimed subject matter has been described with respect to a limited number of embodiments, those skilled in the art, having benefit of this disclosure, will appreciate that other embodiments can be devised which do not depart from the scope of the claimed subject matter as disclosed herein. Accordingly, the scope of the claimed subject matter should be limited only by the attached claims.

What is claimed is:

1. A method for testing fluid comprising:
    providing a bed of unconsolidated sand in a container through which a bore holder is slidably positioned, wherein the bore holder includes a fluid distribution nozzle at a discharge end and the container includes a plurality of perforations;
    compacting the sample in the container and around the bore holder;
    controllably pumping a test fluid through the bore holder and the fluid distribution nozzle;
    withdrawing the bore holder from the container at a predetermined speed to create a simulated well bore;
    receiving a first portion of the test fluid from the simulated well bore in a line in fluid communication with the simulated well bore; and
    receiving a second portion of the test fluid from the perforations in the container.

2. The method of claim 1 wherein the unconsolidated sand is a sample of unconsolidated sand from a well bore.

3. The method of claim 2, further comprising:
    measuring the portion of the test fluid received from the perforations in the container;
    calculating flow permeability of the sample of unconsolidated sand.

4. The method of claim 3 wherein the test fluid is radially distributed to the simulated well bore from the fluid distribution nozzle.

* * * * *